(12) United States Patent
Berry (10) Patent No.: US 6,254,594 B1
(45) Date of Patent: Jul. 3, 2001

(54) DISPOSABLE LIGHT SOURCE FOR PHOTOTHERMAL TREATMENT OF HUMAN TISSUE

(75) Inventor: Michael J. Berry, Pacific Grove, CA (US)

(73) Assignee: Quadrivium, LLC, Phoenix, AZ (US)

(*) Notice: Subject to any disclaimer, the term of this patent is extended or adjusted under 35 U.S.C. 154(b) by 0 days.

(21) Appl. No.: 09/364,955

(22) Filed: Jul. 30, 1999

(51) Int. Cl.[7] .................................................. A61B 18/18
(52) U.S. Cl. ..................... 606/2; 606/3; 606/10; 606/4; 607/88; 607/89; 128/898; 359/333; 359/334; 359/335; 359/342; 359/358; 359/361
(58) Field of Search ................... 606/2, 3–5, 13, 606/17, 41; 128/898; 607/88, 89, 93; 359/333–335, 342, 358–361

(56) References Cited

U.S. PATENT DOCUMENTS

| | | | |
|---|---|---|---|
| 3,074,407 | 1/1963 | Moon et al. | 128/303 |
| 3,575,669 * | 4/1971 | Heaf | 331/94.5 |
| 4,156,124 | 5/1979 | Macken et al. | 219/121 L |
| 4,406,285 | 9/1983 | Villasenor et al. | 128/305 |
| 4,461,294 | 7/1984 | Baron | 128/303.1 |
| 4,608,392 | 8/1986 | Jacquet et al. | 514/844 |
| 4,826,828 | 5/1989 | Wilmott et al. | 514/63 |
| 4,840,175 | 6/1989 | Peyman | 128/303.1 |
| 4,903,695 | 2/1990 | Warner et al. | 606/4 |
| 4,905,711 | 3/1990 | Bennett et al. | 128/869 |
| 4,976,709 | 12/1990 | Sand | 606/5 |
| 5,092,863 | 3/1992 | Schanzlin | 606/5 |
| 5,108,412 | 4/1992 | Krumeich et al. | 606/166 |
| 5,137,530 | 8/1992 | Sand | 606/5 |
| 5,234,957 | 8/1993 | Mantelle | 514/772.6 |
| 5,312,395 | 5/1994 | Tan et al. | 606/9 |
| 5,324,281 * | 6/1994 | Muller | 606/5 |
| 5,336,215 | 8/1994 | Hsueh et al. | 606/4 |
| 5,356,409 | 10/1994 | Nizzola | 606/5 |
| 5,437,657 | 8/1995 | Epstein | 606/4 |
| 5,446,157 * | 8/1995 | Morgan et al. | 546/13 |
| 5,503,165 * | 4/1996 | Schachar | 128/898 |
| 5,582,608 | 12/1996 | Brown | 606/4 |
| 5,616,139 | 4/1997 | Okamoto | 606/4 |
| 5,649,922 | 7/1997 | Yavitz | 606/4 |
| 5,670,547 | 9/1997 | Milstein et al. | 514/725 |
| 5,779,696 * | 7/1998 | Berry et al. | 606/16 |
| 5,846,514 | 12/1998 | Foster et al. | 424/1.81 |
| 5,885,596 | 3/1999 | Parab | 424/401 |
| 6,009,876 * | 1/2000 | Yavitz | 128/898 |

FOREIGN PATENT DOCUMENTS

| | | | |
|---|---|---|---|
| WO 92/01430 | 2/1992 | (WO) | A61F/9/00 |
| WO 95/15134 | 6/1995 | (WO) | A61F/9/00 |

* cited by examiner

Primary Examiner—Linda C. M. Dvorak
Assistant Examiner—Ahmed Farah
(74) Attorney, Agent, or Firm—Fletcher, Yoder & Van Someren (57) ABSTRACT

A system and method for modification of tissue. The system and method utilize a disposable sample cell that contains a chemical mixture capable of photoinitiation. Upon photoinitiation, a chemical reaction creates electromagnetic radiation that is readily absorbed by a desired portion of tissue. The absorption of energy creates heat which can be controlled to result in predetermined modifications to the tissue.

21 Claims, 5 Drawing Sheets

DISPOSABLE LIGHT SOURCE FOR PHOTOTHERMAL TREATMENT OF HUMAN TISSUE

FIELD OF THE INVENTION

The present invention relates generally to a system for improving the shape and/or appearance of an outer layer of tissue, and particularly to the use of a photoinitiated chemical reaction to provide energy for the stimulation of tissue, such as corneal tissue, disposed beneath an outer layer of tissue without damaging the outer layer.

BACKGROUND OF THE INVENTION

Heat has been used to modify and reshape various tissues. For example, lasers, such as carbon dioxide lasers, have been developed and used for the reduction or elimination of wrinkles, such as periorbital wrinkles and other anomalies of the skin. Lasers also have been developed and used for the correction of vision disorders, such as nearsightedness, astigmatism and farsightedness. In thermal keratoplasty, laser light energy has been used to heat the cornea and thereby alter its shape to correct for refractive errors.

The energy from a laser causes conformational changes in collagen and can be used to stimulate the release of factors that promote new collagen growth in the desired area of tissue stimulation, e.g. a subdermal layer of skin. Other laser methods, such as eximer laser photorefractive keratectomy (PRK), also have been utilized for the correction of refractive errors.

Although the use of lasers in correcting refractive errors and improving the appearance of skin has proved to be very promising, laser equipment for such procedures tends to require substantial investment on the part of the hospital, clinic or practitioner using the equipment. It would be advantageous to utilize a source of energy that could be absorbed by the desired tissue, as with laser light energy, but without the substantial expense of the laser equipment.

Another problem that occurs during the heating of desired subsurface tissues to cause tissue modification, is the absorption of energy by the outermost tissue layer, e.g. the epidermis or the epithelial layer of the cornea. As energy, e.g. laser light, passes to the sublayers of the dermis or the cornea where the desired modification or reshaping should occur, undue heating of the outer layers can result. The absorption of energy by the epithelial layer, for example, can damage the epithelium and result in pain, permeability to bacteria, and a wound healing response that is detrimental to the corrective procedure.

It would be advantageous to utilize a less expensive, preferably disposable, source of energy for permanently reshaping sublayers of tissue while reducing the absorption of energy by the outermost layer of tissue.

SUMMARY OF THE INVENTION

The present invention features a method for utilizing an energy source to alter mammalian tissue. The method includes preparing a chemical mixture capable of emitting electromagnetic radiation at a wavelength or wavelengths absorbed by a desired tissue. The electromagnetic radiation is emitted upon photoinitiation of a chemical reaction involving the chemical mixture. The method further includes initiating the chemical reaction, and directing the electromagnetic radiation to the desired tissue.

According to another aspect of the invention, a method is provided for managing a chemical reaction to create a desirable change in a tissue. The method includes combining selected chemicals able to undergo a chemical reaction. The method further includes photoinitiating the chemical reaction to produce energy. Additionally, the method includes exposing a selected tissue to the energy to bring about a desired modification of the selected tissue.

According to another aspect of the present invention, a disposable light source system is provided for use in modification of corneal tissue. The system includes a disposable sample cell containing a chemical mixture. The mixture is able to undergo a chemical reaction that produces energy at a wavelength or wavelengths capable of causing a predetermined modification to a human tissue. The chemical mixture is selected such that the chemical reaction is subject to selective initiation. Additionally, the system includes an outlet aperture in communication with the chemical mixture disposed in the disposable sample cell. A chemical reaction initiator is positioned in communication with the chemical mixture to selectively initiate the chemical reaction. Upon initiation, energy is emitted at the desired wavelength through the outlet aperture.

BRIEF DESCRIPTION OF THE DRAWINGS

The invention will hereafter be described with reference to the accompanying drawings, wherein like reference numerals denote like elements, and.

DETAILED DESCRIPTION OF THE PREFERRED EMBODIMENTS

The present invention relates to a method and system for modifying a target tissue, typically by heating the tissue. The method and system can be used on a variety of tissues, such as subepidermal or subepithelial layers. The system is used to stimulate the release of factors that promote new collagen growth and a thicker healthier matrix of elastins and collagen to provide a younger looking skin. Additionally, the system and method can be utilized to heat and reshape corneal tissue bringing about changes in corneal shape and consequent correction of refractive errors.

Figure 1:
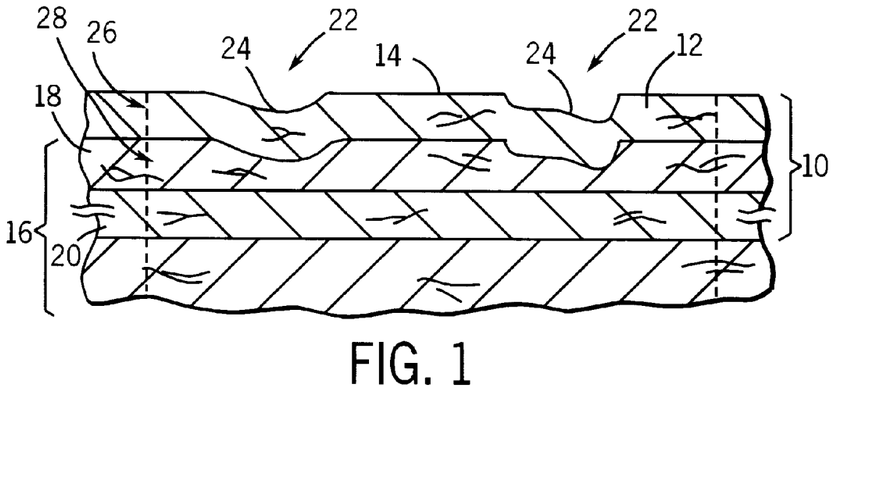
FIG. 1 is a cross-sectional view of a portion of tissue, such as the skin of an individual.

For example, in FIG. 1, a cross-section of a portion of human skin 10 is illustrated. Skin 10 includes an outer epidermal layer or epidermis 12 having an outer surface 14. Outer surface 14 is the visible surface of an individual's skin. Additional tissue 16 is disposed beneath epidermis 12 and includes layers of skin 10 as well as deeper tissue. For example, skin 10 includes a papillary dermis layer 18 disposed between epidermis 12 and a reticular dermis layer 20.

In FIG. 1, skin 10 is illustrated as having an anomaly 22, such as wrinkles 24 disposed along a portion 26 of epidermis 12. By heating an area of tissue disposed beneath portion 26, the anomalies 22 can be lessened or removed to improve the appearance of skin 10. In particular, it is desirable to sufficiently heat a desired treatment area 28 of, for example, papillary dermis layer 18. Sufficient heating of area 28 tends to stimulate the release of factors that promote new collagen growth and the thicker healthier matrix of elastins and collagen. This transformation effectively shrinks or removes wrinkles 12 and provides skin 10 with a younger, healthier appearance.

Figure 2:
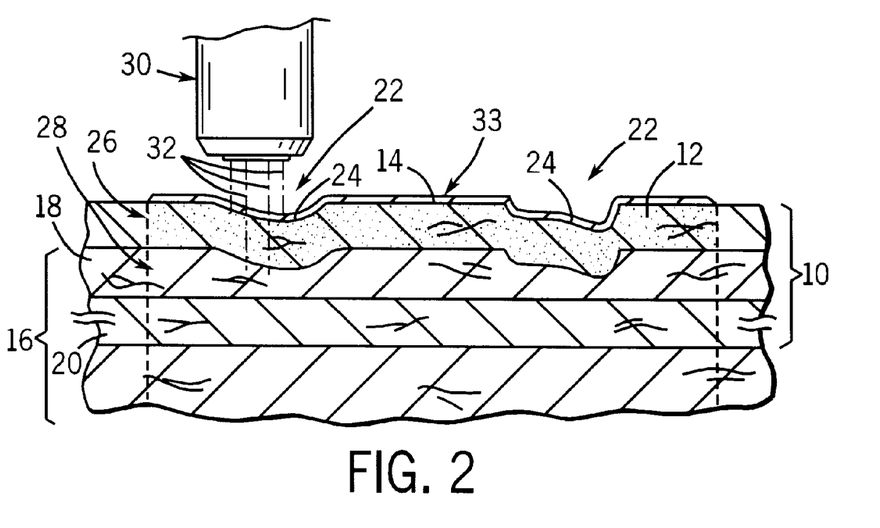
FIG. 2 is a cross-sectional view similar to that of FIG. 1, but showing exemplary regions of tissue undergoing absorption of energy and consequent heating.

According to the present invention, an energy emission system 30 (described in detail below) emits energy in the form of an electromagnetic radiation 32 that can be absorbed by tissue 16 at a specific treatment area 28. The absorption of this energy creates heat within that tissue area.

A common problem in the use of current systems, such as laser based systems, is damage to epidermis 12. Various techniques can be used to reduce this damage, including cooling of the epidermis or the addition of an energy absorption modifier 33 that reduces the absorption of energy by the outer layer of tissue, e.g. epidermis. An exemplary energy absorption modifier 33 is deuterium oxide ($^2H_2^{16}O$), sometimes referred to as deuterated water, an isotopic variant of the naturally occurring water ($^1H_2^{16}O$)disposed in the epidermal layer. Application of the deuterated water effectively changes the absorption spectrum of the outer layer of tissue to permit passage of the electromagnetic radiation with less absorption of energy, as explained below. It should be noted that other isotopic variants, such as $^1H_2^{18}O$, $^{17}O$ variants, partly deuterated water and other isotopic combinations, may be useful for these and other procedures because of their different absorption spectra and the different rates at which they enter into and move out of tissue, namely the pharmacokinetics of the isotopic compounds. Also, some tissues may be amenable to treatment without application of an energy absorption modifier, particularly if the wavelength of the electromagnetic radiation can be selected to largely pass through the outer tissue layer without undue heat generation.

Figures 3, 4A, 4B:
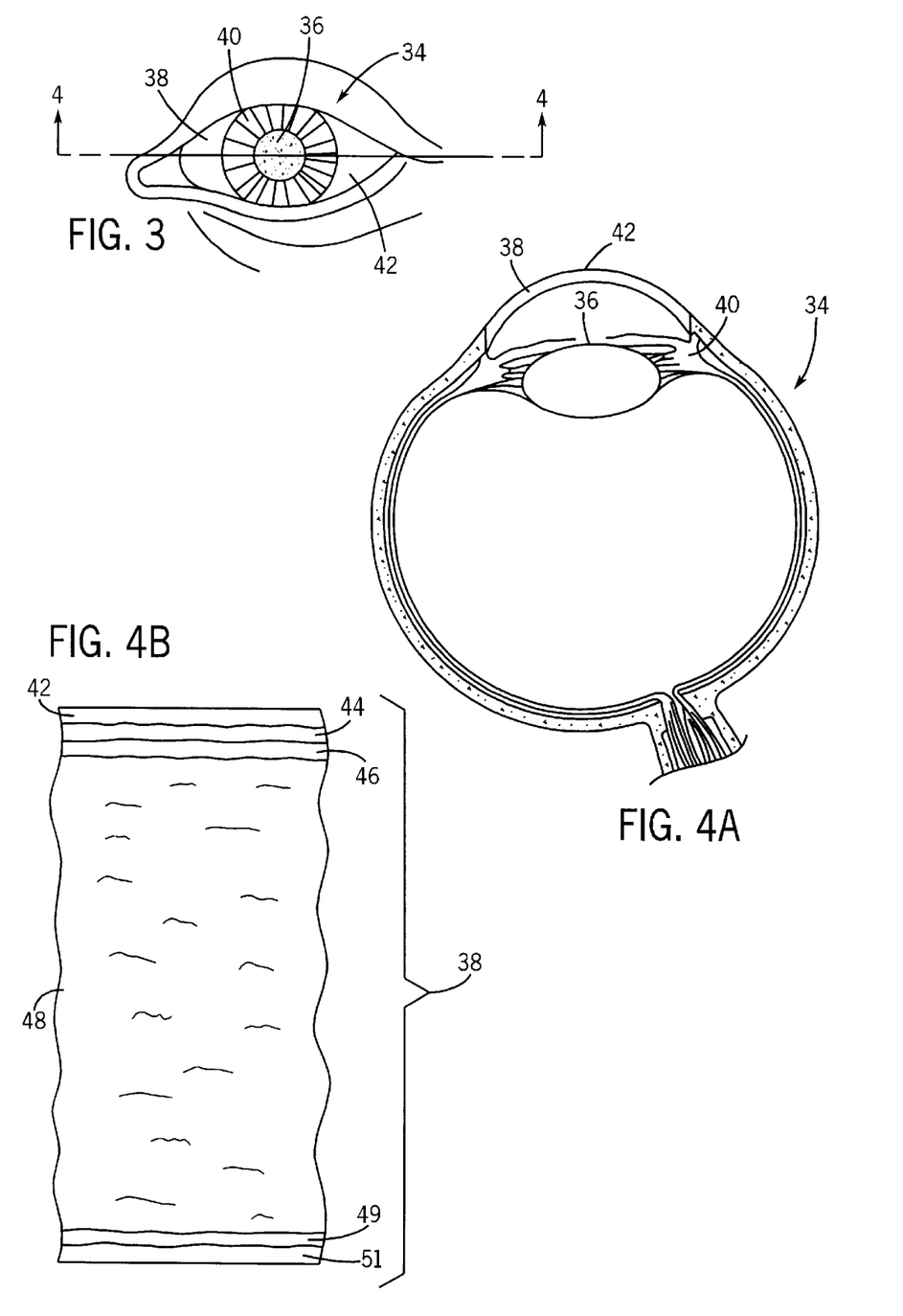
FIG. 3 is a front view of an eye that illustrates corneal tissue that may undergo modification, according to the method and system of the present invention.
FIG. 4A is a cross-sectional view taken generally along line 4—4 of FIG. 3.
FIG. 4B is an enlarged cross-sectional view of a portion of the cornea.

Another exemplary tissue that may be modified via the present inventive system and method is corneal tissue. As illustrated in FIGS. 3 and 4A, an eye 34 includes an aperture, i.e. pupil 36, surrounded by an iris 40. Corneal tissue 38 is disposed radially outward from pupil 36 and is bounded by a corneal surface 42.

Many vision disorders, such as nearsightedness, astigmatism and farsightedness, result from a slightly misshapen corneal surface 42. It has been proved that some of these disorders are correctable by reshaping corneal surface 42 to compensate for the refractive errors causing the sight disorder.

As illustrated in FIG. 4B, eye 34, and particularly corneal tissue 38, includes a plurality of layers between corneal surface 42 and a more central region of the eye that includes, for instance, the lens of the eye. An epithelium or epithelial layer 44 is the outermost tissue layer and bounded by corneal surface 42. Inwardly from epithelial layer 44 is a layer 46, known as Bowman's layer. Radially inward from Bowman's layer 46 is a stroma layer 48 that extends towards the posterior cornea, culminating in Descemet's membrane 49 and the endothelium 51.

By heating a desired region of regions 50 of corneal tissue in the anterior stroma (and especially in Bowman's layer), the tissue structure can be modified to change the curvature of corneal surface 42. To provide the heating, an energy emission system 30, such as that described in FIG. 2, can be used to provide electromagnetic radiation 32, e.g. light energy, to desired region 50. If the electromagnetic radiation characteristics, e.g. wavelength and irradiance, are selected properly, the energy is readily absorbed by specific tissue, e.g. Bowman's layer 46, at the desired region 50. Upon sufficient heating, the shape of the tissue and corneal surface 42 is modified permanently, or at least for a substantial period of the typical recipient's life span.

Desired region 50 usually is disposed beneath corneal surface 42 and typically beneath epithelial layer 44. Depending on the procedure being performed, the desired regions 50 for heating can be at Bowman's layer 46 or at locations beneath Bowman's layer within collagen layer 48. However, there are certain advantages to heating Bowman's layer 46 while reducing or eliminating the absorption of energy by surrounding tissue. Bowman's layer 46 is an a cellular layer that can be modified, via heat from absorption of energy, without initiating the wound healing response that would be typical of the surrounding, cellular tissue.

Figure 5:
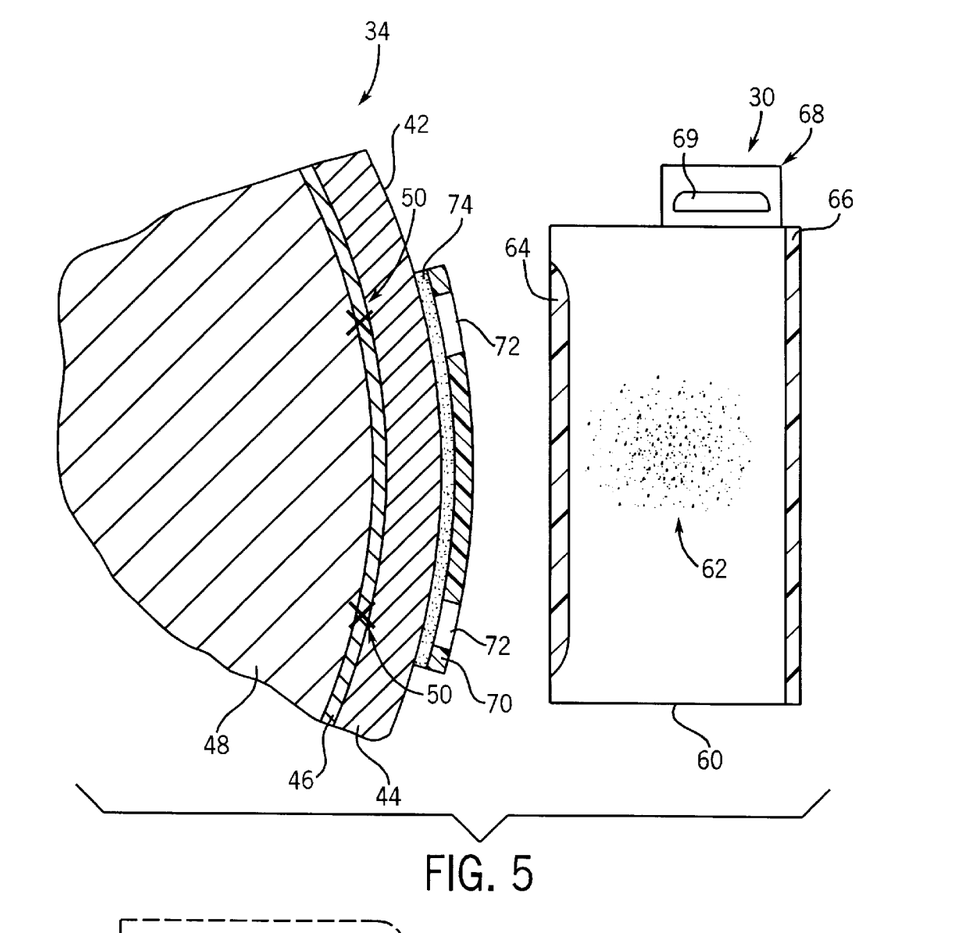
FIG. 5 is a schematic representation of a photocell containing a chemical mixture that can undergo photoinitiation to create energy that may be absorbed by a desired tissue, according to a preferred method of the present invention.

With reference to FIG. 5, an exemplary system and method for modification of tissue is described. In this example, corneal tissue is reshaped through the use of light energy which heats desired regions 50 of the corneal tissue. In the preferred embodiment, the energy for corneal reshaping is produced by a chemical reaction that is initiated by the production of free radicals, e.g. by photoinitiation or electrical-discharge initiation. Specifically, a sample cell 60 contains a chemical mixture 62 that undergoes a chemical reaction upon initiation, preferably upon photoinitiation or electric discharge initiation. As the chemical reaction occurs, electromagnetic radiation in the form of light is produced. This light is then directed to the desired region of tissue, e.g. region 50, for absorption and the consequent heating of the tissue.

Sample cell 60 includes at least one outlet window 64 through which the light passes to the subject tissue. Sample cell 60 typically also includes at least one inlet reflector 66. The chemical reaction can be initiated through the sample cell wall or a window disposed in the wall, unless initiation is caused directly within the chemical mixture by, for instance, an electrical discharge.

In the preferred embodiment, a chemical reaction initiator 68 is disposed in communication with sample cell 60, preferably proximate the side of cell 60. In one embodiment, chemical reaction initiator 68 comprises a light source 69, e.g. an electric flash lamp, such as the Oriel Instruments Model 6427 Xenon Flash Lamp. When light source 69 is lit, light passes through the sidewall of cell 60 and into chemical mixture 62 of sample cell 60. This initiates the desired chemical reaction which produces electromagnetic radiation, such as light energy, of a desired wavelength for absorption by a desired region of tissue. This electromagnetic radiation passes through outlet window 64 and into the subject tissue. Outlet window 64 is preferably a sapphire window. The sapphire window may include a coating, such as a partially reflective coating, that transmits only the desired wavelength or wavelengths of treatment light and that absorbs any undesired light from light source 69. It should be noted that other reaction initiation systems, such as thermal initiation systems or electric discharge initiation systems, potentially can be used.

As illustrated in FIG. 5, a fixture 70 may be placed along corneal surface 42 (or along the surface of other tissue receiving the light energy from sample cell 60) to direct the light energy to the specific desired regions 50 or region 28 for skin treatment. Fixture 70 may have, for example, fenestrations or openings 72 that allow the passage of light only at specific areas. Fixture 70 also may include an applanation window and/or a heat sink to improve treatment of the subepithelial/subepidermal layers while preventing damage to the epithelium/epidermis.

Additionally, an energy absorption modifier 74 may be applied to the outer layer of tissue, e.g. epithelial layer 44, as modifier 33 is applied to epidermis 12. The energy absorption modifiers 33, 74 act to reduce the absorption of energy by the outer tissue layer as the electromagnetic radiation created by the chemical reaction in sample cell 60 passes to the desired region of heating. For example, it may be helpful to displace the naturally occurring water in the epithelial layer, because this water tends to absorb energy at wavelengths utilized in heating regions 50. This water can be replaced by an energy absorption modifier 74, such as deuterium (deuterated water), applied to the epithelial layer 44. Modifiers 33 and 74 diffuse into the epidermal/epithelial layers and the subepidermal (dermal)/subepithelial (stromal) layers, producing a concentration of modifiers versus depth that is a function of time, application of pharmaceuticals, etc.

By way of example, when heating desired regions of Bowman's layer 46, it is desirable to provide light energy within an epithelial transmission "window" that occurs in the 1600–1700 cm$^{-1}$ spectral region. This window refers to the ability of light energy within the suggested spectral region to pass through epithelial tissue while being absorbed by the tissue of Bowman's layer 46 for modification of such tissue. In this spectral region, water is the main absorption chromophore within the epithelium, and has a peak absorption coefficient of 2300 cm$^{-1}$. This absorption coefficient compares with a peak absorption coefficient of approximately 5200 cm$^{-1}$ for Bowman's layer 46 in the same spectral region. Replacement of the naturally occurring water found within the epithelium and Bowman's layer by deuterated water, however, changes the absorption coefficients at ca. 1650 cm$^{-1}$ (aprox:6.1 $\mu$m wavelength) to approximately 150 cm$^{-1}$ and 3000 cm$^{-1}$, respectively. Due to this large difference in deuterated epithelial tissue vs. deuterated Bowman's layer tissue absorption coefficients, it is possible to select an irradiance having a wavelength between 3 $\mu$m and 7 $\mu$m, e.g. approximately 6.0 $\mu$m, that permits strong heating of Bowman's layer with weak absorption of energy and consequent heating of the epithelium. This maintains the epithelium sufficiently cool to prevent significant thermal damage and any resultant wound healing response that can lead to regression of refractive change. For certain applications the preferred wavelength range may be from 3 $\mu$m to 4 $\mu$m and for other applications from 5 $\mu$m to 7 $\mu$m.

Sufficient heating of Bowman's layer 46 to create desired modification of tissue at regions 50 requires that the Bowman's layer tissue is raised to a temperature within or above the collagen phase transition temperature of approximately 58 to 75 degrees Celsius. This heat should be maintained in regions 50 of Bowman's layer 46 for an appropriate length of time. This is particularly true when the epithelial layer 44 is left intact during heating, as described above. In this instance, the irradiation must be comparable to or shorter than the thermal relaxation time for heat conduction from Bowman's layer 46 into the epithelial layer 44. The thermal relaxation time $\tau$ can be estimated from the relation:

$$\tau = \delta^2/4\kappa$$

$\delta$ = thermal diffusion length (cm)
$\kappa$ = thermal diffusivity (cm$^2$/S)

For example if $\delta$ is assumed to be ca. 20 $\mu$m (the approximate thickness of Bowman's layer 46) and $\kappa$ equals 9×10$^{-4}$ cm$^2$/s (a typical value for the cornea), the thermal relaxation time $\tau$ is approximately 1.1 milliseconds.

Therefore, in the specific corneal example described, the light energy pulse emitted from sample cell 60 would be used to radiate the cornea for no longer than 1 millisecond. In fact, it has been determined that irradiation from the light source for a duration of 1 millisecond with a light source having irradiance of approximately 200 w/cm$^2$ is sufficient to cause the subject tissue to undergo the desired modification.

Methods other than use of an absorption modifier 74 may be utilized in reducing the damage and consequent detrimental wound healing response in epithelial layer 44. For example, the corneal epithelium can be removed for an anterior corneal surface treatment by the light energy generated in sample cell 60. This procedure is analogous to photorefractive keratectomy (PRK), but with thermal modification (rather than ablation) of collagen. Alternatively, a microkeratome can be used to form a corneal flap that is folded back to expose the stromal corneal bed for thermal treatment of stromal collagen by light energy emitted from sample cell 60 in a procedure analogous to current LASIK procedures.

To achieve modification of desired regions 50 of Bowman's layer 46, it is desired that a non-laser light source, such as sample cell 60, deliver sufficient light energy at approximately a 6 $\mu$m wavelength on a millisecond time scale, e.g. 1 millisecond. Such electromagnetic radiation is provided by vibrationally excited deuterium bromide (DBr†) formed in the D$_2$/Br$_2$ photoinitiated chemical reaction system:

$Br_2 + \omega \rightarrow 2Br$ $Br + D_2 \rightarrow DBr + D$ $D + Br_2 \rightarrow DBr^\dagger + Br.$ In this system, nonlaser light ($\omega$) is used to photodissociate a portion of Br$_2$ in pre-mixed D$_2$/Br$_2$. The resulting deuterium bromide (DBr) emits light in the 6$\mu$m spectral region in various vibration-rotation transitions. It should be noted that the chemical mixture 62, e.g. D$_2$/Br$_2$, preferably is stored in a container that prevents its premature exposure to light to prevent pre-reaction. Also, an inert gas, such as helium, may be added to the mixture 62 to modify reaction rates and/or the relative amounts of DBr emission in various vibration-rotation transitions.

There are other energy sources, specifically light sources, that are useful for various tissue modification procedures. For example, in various procedures for photothermal keratoplasty (PTK), the corneal epithelium is either removed or a corneal epithelial flap is formed to expose Bowman's layer for irradiation. In these procedures, sample cell 60 may utilize a different chemical mixture to produce the light energy for desired tissue modification. Sufficient light can be produced using the $H_2/Cl_2$ and $H_2/O_2$ chain reactions. Preferably, these reactions are initiated by photodissociation of $Cl_2$ in the case of the $H_2/Cl_2$ photochemical chain reaction, or by an electric discharge or spark in the case of the $H_2/O_2$ explosion reaction. A nonlaser light source that delivers sufficient light energy for PTK at ca. 3–4 μm wavelength on a millisecond time scale is vibrationally excited hydrogen chloride ($HCl^\backslash$) formed in the $H_2/Cl_2$ photoinitiated chemical reaction system set forth below:

$$Cl_2+\omega \rightarrow 2Cl$$

$$Cl+H_2 \rightarrow HCl+H$$

$$H+Cl_2 \rightarrow HCl^\backslash+Cl.$$

Nonlaser light (ω) is used to photodissociate a portion of $Cl_2$ in premixed $H_2/Cl_2$. As described above, this mixture should be stored in sample cell 60 in the dark to prevent pre-reaction. Alternatively, various pre-radical scavengers, such as ethylene, can be added to the chemical mixture in concentrations sufficient to prevent chain propagation and pre-reaction.

Figure 6:
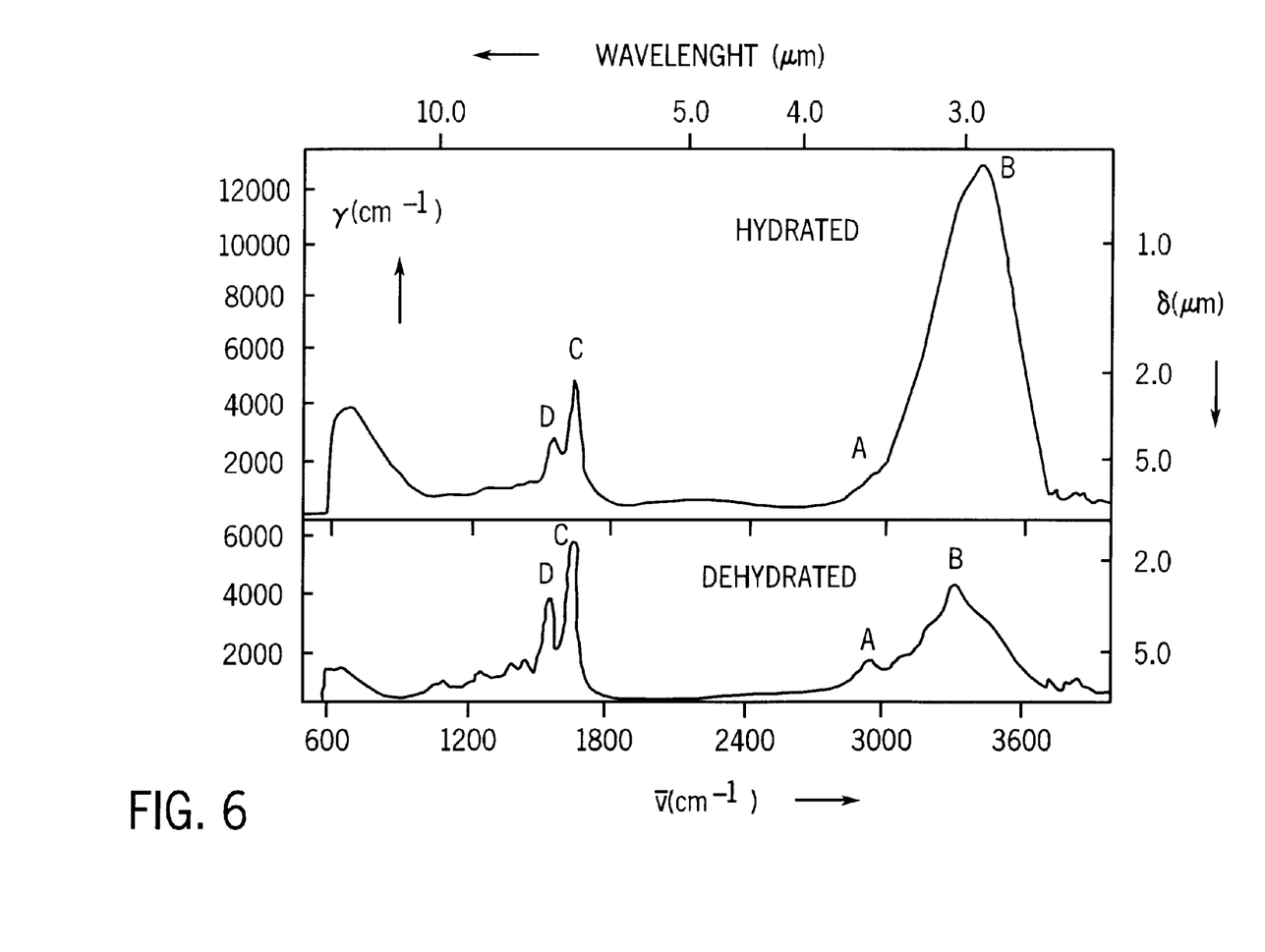
FIG. 6 is a graphical illustration of absorption spectra of hydrated and dehydrated corneal stromal tissue.

$HCl^\backslash$ emits light in the 3–4 μm spectral region in various vibration-rotation transitions. This spectral region is appropriate for heating corneal tissue, such as Bowman's layer, using CH-stretch absorption features that have large absorption coefficients. As illustrated in FIG. 6, region A of the graph shows the infrared absorption spectra of hydrated and dehydrated corneal stromal tissue.

Another nonlaser light source that delivers sufficient energy for tissue modification, such as that required in PTK, is vibrationally excited hydroxyl radical ($OH^\backslash$) and vibrationally excited water $H_2O^\backslash$ formed in the $H_2/O_2$ electrical-discharge-initiated chemical reaction system that follows:

$$H_2+e- \rightarrow 2H+e-$$

$$O_2+e- \rightarrow 2O+e-$$

$$O+H_2 \rightarrow OH+H$$

$H+O_2+M \rightarrow HO_2+M$ (where M is a third body) . . . (+ several other elementary reactions) . . .

Overall reaction: $2H_2+O_2 \rightarrow 2H_2O+457.4$ kJ/mole ($O_2$). Placing the above chemical mixture in sample cell 60 and initiating the overall reaction produces sufficient light energy at ca. 2.6–3 μm wavelength on an appropriate millisecond time scale.

The above described reaction preferably is initiated by an electrical discharge that is used to produce electrons ($e^-$) that dissociate $H_2$ and $O_2$. The resulting combustion reaction ultimately yields "hot" $H_2O^\backslash$ (and "hot" $OH^\backslash$) that radiate their vibrational energy principally in the 2.5–3 μm spectral region. This spectral region is appropriate for heating corneal tissue, such as Bowman's layer, using NH-stretch and O—H stretch absorption features that have large absorption coefficients. This absorption region is illustrated by region B of FIG. 6 which shows the infrared absorption spectra of hydrated and dehydrated corneal stromal tissue.

It also should be noted that the chemical mixture and reaction described above to produce $DBr^\backslash$ emission for corneal reshaping uses the collagen type I amide absorption feature, illustrated by region C in FIG. 6. This reaction can be initiated with other photoinitiated chemical reactions and/or electrical discharge to produced, for example, vibrationally excited carbon monoxide ($CO^\backslash$) that radiates at least a portion of its energy in the approximately 6 μm spectral region. For example, a suitable reaction system is the $CS_2/O_2$ reaction system where CS and O radicals are produced by an electrical discharge, leading to the subsequent formation of $CO^\backslash$ in the CS+O reaction:

$$CS_2+e- \rightarrow CS+S+e-$$

$$O_2+e- \rightarrow 2O+e-$$

$$O+CS \rightarrow CO^\backslash+S$$

The above-listed methods for initiating desired chemical reactions typically involve the release of free radicals to initiate the reaction. Furthermore, there may be other chemical mixtures and chemical reaction initiation methods, as well as other absorption regions, such as region D illustrated in FIG. 6, that can provide a ready source of nonlaser light for modification of tissue.

Figure 7:
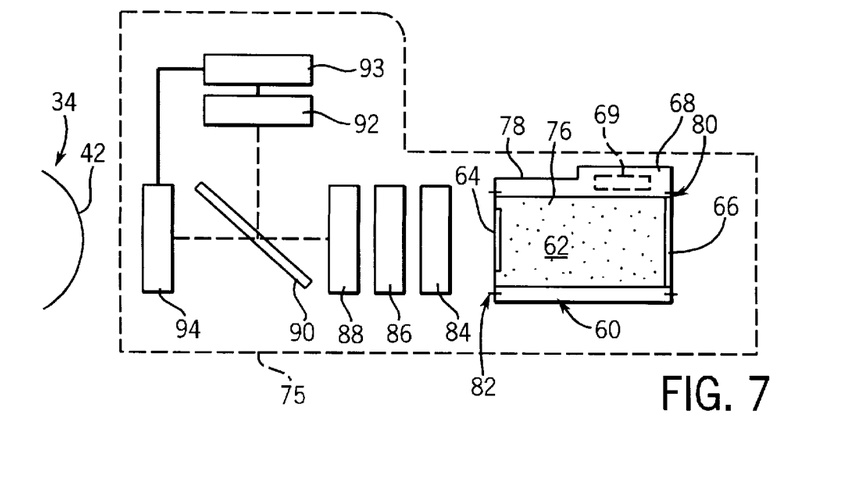
FIG. 7 is a schematic representation of a disposable light source system, according to one embodiment of the present invention.

Referring to FIG. 7, an exemplary system 75 is illustrated for utilizing the energy produced by a photoinitiated chemical reaction to induce modification of tissue. The system described is an exemplary system for modification of corneal tissue, such as regions of Bowman's layer. However, this system and method of modifying desired tissues can be utilized for a variety of tissue regions.

As illustrated, sample cell 60 comprises a disposable sample cell 76 that contains the desired chemical mixture 62. For example, chemical mixture 62 may comprise the mixture of $D_2$, $Br_2$, and an inert gas, such as helium (He), described above. The disposable sample cell 76 includes outlet window 64, preferably a sapphire or calcium fluoride ($C_aF_2$) window, to transmit electromagnetic radiation in the form of light at approximately 6 μm. The light is emitted by the vibrationally excited deuterium bromide ($DBr^\backslash$) that results from the chemical reaction initiated by light source 69. The disposable sample cell 76 also may include the reflector 66 to facilitate reflection of light through outlet window 64.

Preferably, disposable sample cell 76 is mounted within a container 78 that prevents premature exposure of disposable sample cell 76 and its chemical constituents to light. Container 78 includes an inlet aperture 80 to permit entrance of the light from light source 69. Container 78 also includes an outlet aperture 82 that permits the egress of light emitted from disposable sample cell 76 as a result of the internal chemical reaction.

The overall system further includes an integrating sphere apparatus 84 coupled in communication with disposable sample cell 76. Integrating sphere apparatus 84 is disposed downstream from the sapphire window 64 and may be integral with sample cell container 78.

A light pipe 86 preferably is used to channel the approximately 6 μm light to the cornea. Typically, light pipe 86 is internally coated with a diffuse gold coating. A filter 88, such as the Optical Coating Laboratory, Inc., Model LO 5887-8 Long Wavelength Pass Filter, is used to prevent light of wavelengths shorter than ca. 5.8 μm from irradiating the cornea.

Typically, the combination of integrating sphere apparatus 86 and filter 88 yield uniform irradiance to the cornea. However, a mask, e.g. fixture 70, with fenestrations 72 can be utilized in ensuring desired spatial patterns of transmission to provide the proper pattern of corneal irradiation for correction of a predetermined refractive error of the cornea. Fixture 70 may also comprise, for example, windows having partially transmitting coatings with desired spatial patterns.

The overall system further includes a calibrated beam splitter 90, a photodetector 92, a computer/controller 93 and a shutter assembly 94. The calibrated beam splitter 90, photodetector 92 and shutter assembly 94 preferably are disposed at an end of light pipe 86 opposite disposable sample cell 76 and proximate the tissue, e.g. corneal tissue, to be irradiated. The combination of the calibrated beam splitter 90, photodetector 92, computer/controller 93 and shutter assembly 94 provides for accurate irradiation of, for example, the cornea with approximately 6 $\mu$m light.

In this embodiment, a portion of the light passing through light pipe 86 is directed by calibrated beam splitter 90, preferably a sapphire window, onto photodetector 92, such as the Oriel Instruments Model 70777 HgCdZnTe detector. The photodetector 92 and the computer/controller 93 are used to measure the integrated light vs. time. This measurement then is used by the computer/controller 93 to provide an electrical signal for opening and closing shutter assembly 94. An exemplary shutter is an electromechanical shutter, such as the Vincent Associates Uniblitz electromechanical shutter. This combination of components is one preferred way of achieving extremely accurate control over the total delivered light energy to the subject tissue.

Figure 8:
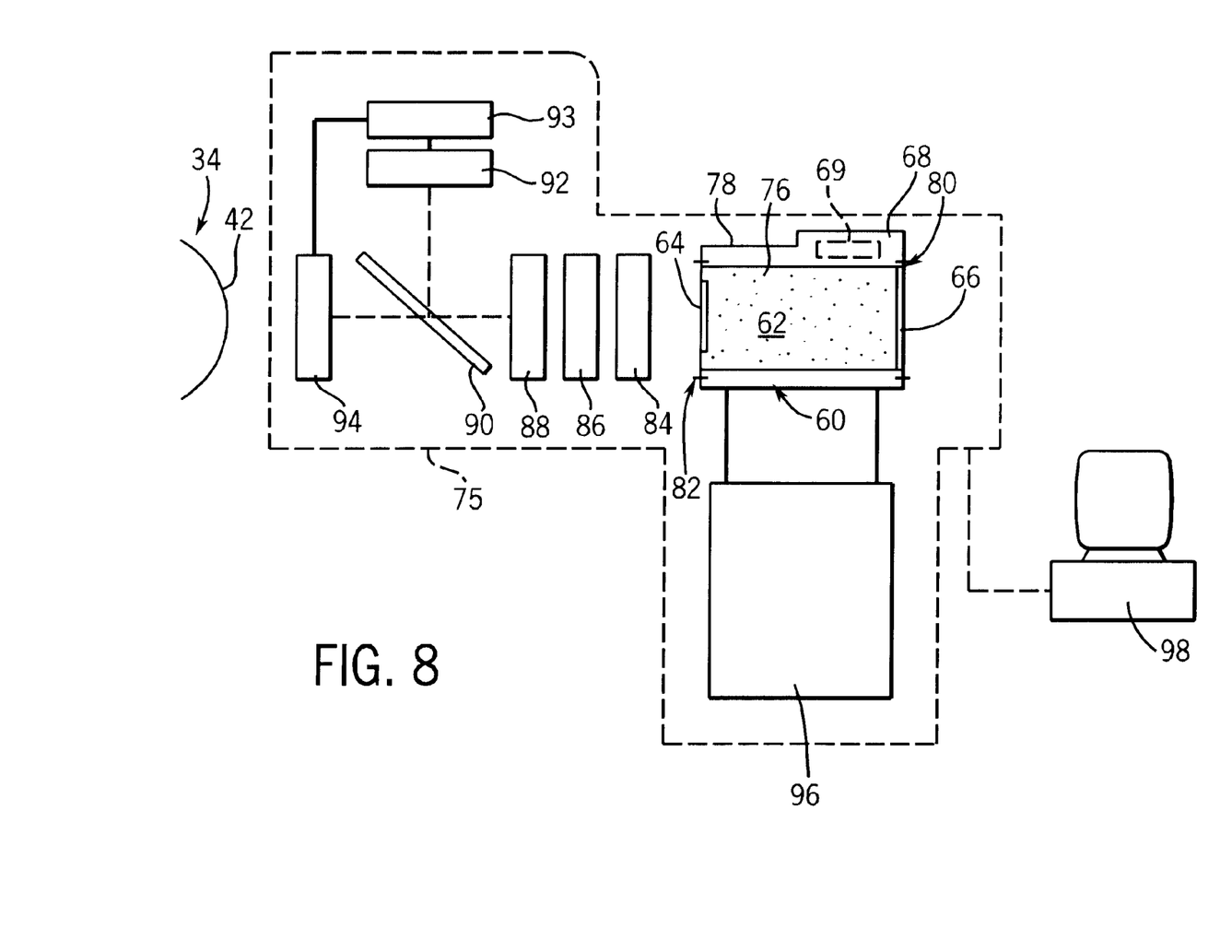
FIG. 8 is a schematic illustration of an alternate embodiment of the system illustrated in FIG. 7.

In an alternate embodiment, such as that illustrated in FIG. 8, additional components may be added to the overall system. For example, an automated sample cell handler 96 may be used to remove spent disposable cells 76 and to supply a fresh disposable sample cell 76 for the next procedure. Additionally, a computer control, such as a personal computer 98, may be connected to the system for initiation and control of the delivered light as well as for record keeping, such as procedure details related to individual patients.

In operation, the system is easy and inexpensive to utilize in carrying out the method of modifying a desired tissue, such as desired regions of Bowman's layer in the human cornea. A disposable sample cell 76 is selected with an appropriate chemical mixture for producing electromagnetic radiation at a desired wavelength for a given procedure. The sample cell 76 is disposed within container 78 and a chemical reaction between its chemical constituents is initiated, e.g. photoinitiated, by light source 69.

The chemical reaction produces electromagnetic radiation, e.g. light having a wavelength of approximately 6 $\mu$m, that is emitted through sapphire window 64. The emitted light is further channeled through integrating sphere apparatus 84, light pipe 86 and filter 88 and directed to the tissue to be treated, e.g. corneal tissue regions 50.

The total delivered light energy (the amount of light energy delivered over time) is controlled by beam splitter 90, photodetector 92, computer/controller 93 and shutter assembly 94 to provide, for example, irradiation of a cornea with ca. 0.1 Joules of approximately 6 $\mu$m light within a 1–2 millisecond period to achieve desired corneal reshaping. It also should be noted that the partial and total pressure of the mixture ($D_2$, $Br_2$, He) may be varied to optimize the output of 6 $\mu$m light within the desired time "window" for corneal reshaping without damage to the epithelial layer.

It will be understood that the foregoing description is of preferred exemplary embodiments of this invention and that the invention is not limited to the specific forms shown. For example, the system and method may be utilized on bodily tissues other than those of the eye or skin. Components may be added, altered or removed from the system depending on the desired application of the initiated chemical reaction to modify tissue; the disposable sample cell may be prepared in a variety of configurations and in a variety of packages; the chemical mixture may be altered or changed depending on the desired emission of radiation and the absorption properties of the target tissue areas; and the disposable sample cell may be formed as part of its container or readily insertable and removable from its light-tight container. These and other modifications may be made in the design and arrangement of the elements without departing from the scope of the invention as expressed in the appended claims.

What is claimed is:

1. A disposable light source system for use in modification of tissue, comprising:

a disposable sample cell containing a chemical mixture able to undergo a chemical reaction that produces energy at a desired wavelength capable of causing a desired modification to a human tissue, the chemical reaction being subject to initiation by the releasing of free radicals;

an outlet aperture in communication with the chemical mixture; and a chemical reaction initiator positioned in communication with the chemical mixture to selectively initiate the chemical reaction, wherein upon initiation, energy at the desired wavelength is emitted through the outlet aperture.

2. The disposable light source system as recited in claim 1, wherein the chemical mixture reacts to emit light energy at a wavelength in the range from approximately 3 $\mu$m to approximately 4 $\mu$m.

3. The disposable light source system as recited in claim 1, wherein the chemical mixture reacts to emit light energy at a wavelength in the range from approximately 5 $\mu$m to approximately 7 $\mu$m.

4. The disposable light source system as recited in claim 1, further comprising an energy absorption modifier applied to the tissue.

5. The disposable light source system as recited in claim 4, wherein the energy absorption modifier comprises an isotopic variant of naturally occurring water.

6. The disposable light source system as recited in claim 1, wherein the chemical mixture comprises $Br_2$ and $D_2$.

7. The disposable light source system as recited in claim 6, wherein the chemical reaction initiator comprises an electronic flash lamp.

8. The disposable light source system as recited in claim 7, wherein the sample cell includes a $CaF_2$ window to transmit energy at the desired wavelength.

9. The disposable light source system as recited in claim 7, wherein the sample cell includes a sapphire window to transmit energy at the desired wavelength.

10. The disposable light source system as recited in claim 9, further comprising an integrating sphere apparatus disposed in communication with the sample cell; and a light pipe disposed in communication with the integrating sphere apparatus to direct the energy of the desired wavelength to the human tissue.

11. The disposable light source system as recited in claim 10, further comprising a filter to filter from the energy emitted radiation having wavelengths shorter than approximately 5.8 $\mu$m.

12. The disposable light source system as recited in claim 11, further comprising a shutter assembly to control the time period over which the energy is delivered to the human tissue.

13. A method for utilizing an energy source to alter mammalian tissue comprising:

preparing a chemical mixture capable of emitting an electromagnetic radiation at a wavelength absorbed by a desired tissue, the electromagnetic radiation being emitted upon initiation of a chemical reaction;

photoinitiating the chemical reaction; and directing the electromagnetic radiation to the desired tissue;

wherein the photoinitiating includes exposing the chemical mixture to a flash of light, further wherein preparing includes selecting the chemical mixture to emit light energy at a wavelength in the range from approximately 5 $\mu$m to approximately 7 $\mu$m.

14. The method as recited in claim 13, further comprising:

heating a selected corneal tissue to at least approximately 58° C.

15. A method for utilizing an energy source to alter mammalian tissue, comprising:

preparing a chemical mixture capable of emitting an electromagnetic radiation at a wavelength absorbed by a desired tissue, the electromagnetic radiation being emitted upon initiation of a chemical reaction;

initiating the chemical reaction; and directing the electromagnetic radiation to the desired tissue;

wherein initiating comprises photoinitiating, and photoinitiating comprises exposing the chemical mixture to a flash of light, wherein selecting includes selecting the chemical mixture to emit light energy at a wavelength in the range from approximately 3 $\mu$m to approximately 4 $\mu$m.

16. The method as recited in claim 15, further comprising heating a selected corneal tissue to at least approximately 58° C.

17. A method for utilizing an energy source to alter mammalian tissue, comprising:

preparing a chemical mixture capable of emitting an electromagnetic radiation at a wavelength absorbed by a desired tissue, the electromagnetic radiation being emitted upon initiation of a chemical reaction;

initiating the chemical reaction; and directing the electromagnetic radiation to the desired tissue, wherein preparing comprises mixing $D_2$ and $Br_2$.

18. A method for managing a chemical reaction to create a desirable change in a tissue, comprising:

combining selected chemicals able to undergo a chemical reaction;

photoinitiating the chemical reaction to produce energy; and exposing a selected tissue to the energy to bring about a desired modification of the selected tissue, wherein combining includes creating a chemical mixture containing $D_2$ and $Br_2$.

19. The method as recited in claim 18, wherein photoinitiating comprises exposing the combined, preselected chemicals to a flash of light.

20. A method for managing a chemical reaction to create a desirable change in a tissue, comprising:

combining selected chemicals able to undergo a chemical reaction;

photoinitiating the chemical reaction to produce energy; and exposing a selected tissue to the energy to bring about a desired modification of the selected tissue, wherein combining comprises selecting a chemical mixture that emits radiation having a wavelength in the range from approximately 5 $\mu$m to approximately 7 $\mu$m following photoinitiation of the chemical reaction.

21. A method for managing a chemical reaction to create a desirable change in a tissue, comprising:

combining selected chemicals able to undergo a chemical reaction;

photoinitiating the chemical reaction to produce energy; and exposing a selected tissue to the energy to bring about a desired modification of the selected tissue, wherein combining includes selecting the chemical mixture to emit light energy at a wavelength in the range from approximately 3 $\mu$m to approximately 4 $\mu$m.

* * * * *